United States Patent
Gregoire et al.

(10) Patent No.: US 10,907,199 B2
(45) Date of Patent: Feb. 2, 2021

(54) DOUBLE-STRAND DNA BREAK QUANTIFICATION METHOD

(71) Applicant: SOCIETE DE COMMERCIALISATION DES PRODUITS DE LA RECHERCHE APPLIQUÉE SOCPRA, Sherbrooke (CA)

(72) Inventors: Marie-Chantal Gregoire, Sherbrooke (CA); Guylain Boissonneault, Sherbrooke (CA); Frédéric Leduc, Candiac (CA); Julien Massonneau, Sherbrooke (CA); Olivier Simard, Sherbrooke (CA); Chloé Lacombe-Burgoyne, Montréal (CA)

(*) Notice: Subject to any disclaimer, the term of this patent is extended or adjusted under 35 U.S.C. 154(b) by 0 days.

(21) Appl. No.: 16/167,781

(22) Filed: Oct. 23, 2018

(65) Prior Publication Data

US 2019/0161792 A1    May 30, 2019

(30) Foreign Application Priority Data

Oct. 27, 2017  (CA) .................... 2984019

(51) Int. Cl.
  *C12Q 1/6851*  (2018.01)
  *C12Q 1/686*   (2018.01)
  *C12Q 1/6827*  (2018.01)

(52) U.S. Cl.
  CPC ........... *C12Q 1/6851* (2013.01); *C12Q 1/686* (2013.01); *C12Q 1/6827* (2013.01); *C12Y 207/07007* (2013.01); *C12Y 207/07031* (2013.01); *C12Y 605/01001* (2013.01)

(58) Field of Classification Search
  None
  See application file for complete search history.

(56) References Cited

PUBLICATIONS

Leduc et al. (PLOS One 2011 vol. 6 e17353) (Year: 2011).*
A.G. Basnakian, J.S. James, Quantification of 3'-OH DNA breaks by random oligonucleotide-primed synthesis (ROPS) assay, DNA Cell Biol. 15 (1996) 255-262.
N. Crosetto et al., Nucleotide-resolution DNA double-strand break mapping by next-generation sequencing, Nat. Methods 10 (2013) 361-365.
S. Rodrigue et al., Unlocking short read sequencing for metagenomics, PLoS One 5 (2010) e11840.
H. Li, R. Durbin, Fast and accurate short read alignment with Burrows-Wheeler transform, Bioinformatics 25 (2009) 1754-1760.
Picard Tools—By Broad Institute. sur <http://broadinstitute.github.io/picard.>Accessed on Jun. 16, 2016.
I. Milne et al., Using Tablet for visual exploration of second-generation sequencing data, Brief. Bioinf. 14 (2013) 193-202.
F. Peyresaubes et al., Immuno-capture of UVDE generated 3'-OH ends at UV photoproducts, DNA Repair (Amst.) 36 (2015) 156-161.
Grégoire MC, Massonneau J, Leduc F, Arguin M, Brazeau MA, Boissonneault G, Quantification and genome-wide mapping of DNA double-strand breaks, DNA Repair (Amst). Dec. 2016;48:63-68. doi: 10.1016/j.dnarep.2016.10.005. Epub Oct. 29, 2016.

* cited by examiner

*Primary Examiner* — Katherine D Salmon
(74) *Attorney, Agent, or Firm* — Marie-Helene Rochon

(57) ABSTRACT

The present disclosure provides the quantification of double-strand breaks in DNA molecules using terminal deoxynucleotidyl transferase using a preliminary step of nick gap and repair. This preliminary step comprising contacting the DNA molecules with both a DNA ligase and a DNA polymerase to repair DNA nicks and remove DNA gaps prior to using the terminal deoxynucleotidyl transferase.

19 Claims, 7 Drawing Sheets

DOUBLE-STRAND DNA BREAK QUANTIFICATION METHOD

TECHNOLOGICAL FIELD

This disclosure concerns methods for quantifying double-strand DNA breaks based on the use to labelling 3'-OH free termini generated by the double-strand DNA breaks.

BACKGROUND

The genotoxic character of DNA double-strand breaks (DSBs) is well known as they may lead to genomic rearrangements, cell death or cancer if left unrepaired. Most DSBs arise from endogenous mechanisms but may also be produced as a result of ionizing radiation or chemotherapy. Although some endogenous DSBs are generated accidentally such as those resulting from DNA replication failure, many cellular processes require controlled DSBs formation such as transcription initiation, meiotic recombination, chromatin remodeling or V(D)J recombination.

Establishing both the number and physical distribution of DSBs would allow for a better study of the repair kinetic and the consequences of the repair processes within gene related sequences or intergenic regions. In the clinical setting this should provide a straightforward determination of genetic stability for a given tissue. Available methods to detect DSBs include indirect determination like immunofluorescence against markers such as γH2AFX or DSB repair proteins combined with microscopy, flow cytometry or chromatin immunoprecipitation. These techniques probably underestimate the extent of DSBs as they use antibodies to detect proteins bound to DSB and are found as foci only at sites where active DSB repair proceeds. Non-canonical functions have however been recently associated with γH2AFX such as DNA single strand break (SSB) repair and chromatin remodeling. Direct techniques to detect DSBs include electrophoresis in neutral conditions such as single cell electrophoresis (comet) assay and pulsed field gel electrophoresis. These techniques suffer from an obvious lack of sensitivity because DSBs must be present in a significant fraction of the cells and occur at several loci per cell in order to observe an increase in DNA mobility, whereas rare breaks within high molecular weight DNA can hardly be detected. In addition to being cumbersome and costly, these techniques can hardly be standardized between labs. Although direct labeling of 3'-OH DNA ends with enzymes and reporter molecules represent a sensitive method, specific and total labeling of DSBs has so far not been achieved.

There is thus a need to provide a method for determining the presence and preferably the number of double-strand DNA breaks. It would also be advisable to provide a method capable, in some embodiments, of locating the double-strand DNA breaks within the genome. The method would preferably be conducted on isolated DNA molecules.

BRIEF SUMMARY

The present disclosure provides the quantification, and optionally the location of double-strand breaks in DNA molecules using terminal deoxynucleotidyl transferase as well as a preliminary step of nick gap and repair. This preliminary step comprising contacting the DNA molecules with both a DNA ligase and a DNA polymerase to repair DNA nicks and remove DNA gaps prior to using the terminal deoxynucleotidyl transferase.

In a first aspect, the present disclosure provides a method for quantifying double-stand breaks in a sample comprising DNA molecules susceptible of having at least one DNA nick, at least one DNA gap and at least one DNA double strand break. Broadly the method comprises (a) contacting the sample with a DNA ligase and a DNA polymerase under conditions to (i) allow reparation of the at least one DNA nick and the at least one DNA gap, (ii) inhibit the amplification of the DNA molecules and (iii) obtain a first DNA mixture comprising first DNA molecules having a 3'-OH free terminus; (b) contacting the first DNA mixture with a terminal deoxynucleotidyl transferase (TdT) and a substrate of the TdT, said substrate comprising a nucleotide having a label, under conditions so as to allow the incorporation of the nucleotide at the 3'-OH free terminus of the first DNA molecules to obtain a second DNA mixture comprising second DNA molecules having the incorporated nucleotide; (c) purifying second DNA molecules from the second DNA mixture to obtain substantially isolated DNA molecules; (d) optionally amplifying, arraying and/or sequencing the substantially isolated DNA molecules obtained at step (c); and (e) quantifying a signal associated with the label of the substantially isolated DNA molecules obtained at step (c), the amplification of the substantially isolated DNA molecules obtained at step (d), the array of the substantially isolated DNA molecules obtained at step (d) and/or the sequence of the substantially isolated DNA molecules obtained at step (d) to quantify and optionally locate DNA double-strand breaks in the sample. In an embodiment, the sample comprises isolated DNA molecules and the method can further comprise, for example, isolating DNA molecules from the sample prior to step (a). In an embodiment, the method can lack purifying the first DNA molecules between steps (a) and (b) (e.g., the first DNA mixture is used directly in step (b) to generate the second DNA mixture). In an embodiment, the DNA ligase is a T4 DNA ligase. In another embodiment, the DNA polymerase is a T4 DNA polymerase. In yet another embodiment, the conditions used in step (a) comprise including adenosine triphosphate (ATP) at a concentration of less than about 10 µM in a buffer for the DNA ligase and/or for the DNA polymerase. In still another embodiment, the conditions used in step (a) comprise using a single buffer for contacting the sample with the DNA ligase and the DNA polymerase. In an embodiment, the method comprises, at step (c), positively selecting the second DNA molecules from the second DNA mixture to obtain substantially isolated DNA molecules. This can be done, for example, by using a silanol-based solid support to positively select the second DNA molecules from the second DNA mixture. In an embodiment, the label is a radioactive isotope and, in another embodiment, the nucleotide can be a terminator nucleotide. In such embodiment, the method can comprise, at step (e), quantifying the radioactivity in the substantially isolated DNA molecules to quantify DNA double-strand breaks in the sample. In another embodiment, the label is an enzyme. In such embodiment, the method can comprise, at step (e), quantifying the enzymatic activity of the enzyme in the substantially isolated DNA molecules to quantify DNA double-strand breaks in the sample. In still another embodiment, the label is a light-emitting entity. In such embodiment, the method can comprise, at step (e), quantifying the light emitted by the light-emitting entity in the substantially isolated DNA molecules to quantify DNA double-strand breaks in the sample. In yet another embodiment, the label is a prosthetic group, such as, for example a biotin group. In an embodiment, the method comprises performing step (d). In another embodiment, the method comprises at step (c), performing a salt precipitation or an electrophoretic purification to purify the second DNA molecules from the second DNA mixture. In still another embodiment, the method further comprises, prior to step (d), fragmenting with a fragmenting enzyme the substantially isolated DNA molecules to provide fragmented DNA molecules and, at step (d), quantifying a signal associated with the fragmented DNA molecules to quantify DNA double-strand breaks in the sample. The fragmenting enzyme can be, for example, a Taq$^{\alpha 1}$, a double-strand DNA Shearase™ and/or a Fragmentase®. In an embodiment, the method comprises using a solid support to positively select the fragmented DNA molecules comprising the incorporated nucleotide from the fragmented DNA molecules to provide isolated, fragmented and labeled DNA molecules. In such embodiment, the solid support can comprise an antibody specific for the label. In another embodiment, the method can comprise, at step (d), amplifying the isolated, fragmented and labeled DNA molecules and, at step (e), quantifying the signal associated with the isolated, amplified fragmented and labeled DNA molecules to quantify and optionally localize the DNA double-strand breaks in the sample. This can be done, for example, by using quantitative PCR to amplify the isolated, fragmented and labeled DNA molecules. In another embodiment, the method can comprise, at step (d), sequencing the isolated, fragmented and labeled DNA molecules and, at step (e) quantifying the signal associated with the isolated, sequenced fragmented and labeled DNA molecules to quantify and optionally localize the DNA double-strand breaks in the sample. This can be done, for example, using next generation sequencing to sequence the isolated, fragmented and labeled DNA molecules. In another embodiment, the nucleotide is a terminator nucleotide.

In a second aspect, the present disclosure provides a kit for quantifying double-stand breaks in a sample comprising DNA molecules susceptible of having at least one DNA nick, at least one DNA gap and at least one DNA double strand break. The kit can comprise a DNA ligase, a DNA polymerase, a terminal deoxynucleotidyl transferase (TdT), a substrate for the TdT, the substrate comprising a nucleotide having a label and/or instructions to perform the steps defined herein.

Abbreviations Used in This Disclosure:
DSB DNA double-strand break
SSB DNA single-strand break
TdT terminal deoxynucleotidyl transferase
NGR DNA nick and gap repair
dBrIC DNA break immunocapture
qTUNEL quantitative TUNEL;
NGS next-generation sequencing
% IP percentage of immunoprecipitation (IP/input)
DBrIC-Seq DNA break immunocapture followed by next-generation sequencing

BRIEF DESCRIPTION OF THE DRAWINGS

Having thus generally described the nature of the invention, reference will now be made to the accompanying drawings, showing by way of illustration, a preferred embodiment thereof, and in which:

FIG. 2 provide a determination of potential TdT-labeling at mechanical DNA breaks.

FIG. 3 provide the sensitivity of DBrIC and qTUNEL after NGR.

FIG. 4A shows the Dig(−), Undigested HeLa-I-SceI DNA.

FIG. 4B shows the Nicked, Nt.BbvCI-digested HeLa-I-SceI DNA.

FIG. 4C shows the DSB, I-SceI-digested HeLa-I-SceI DNA. Upper track shows coverage and lower track represents individual reads.

FIG. 5 provide the constructions used for the HeLa-I-SceI model.

DETAILED DESCRIPTION

Figure 1:
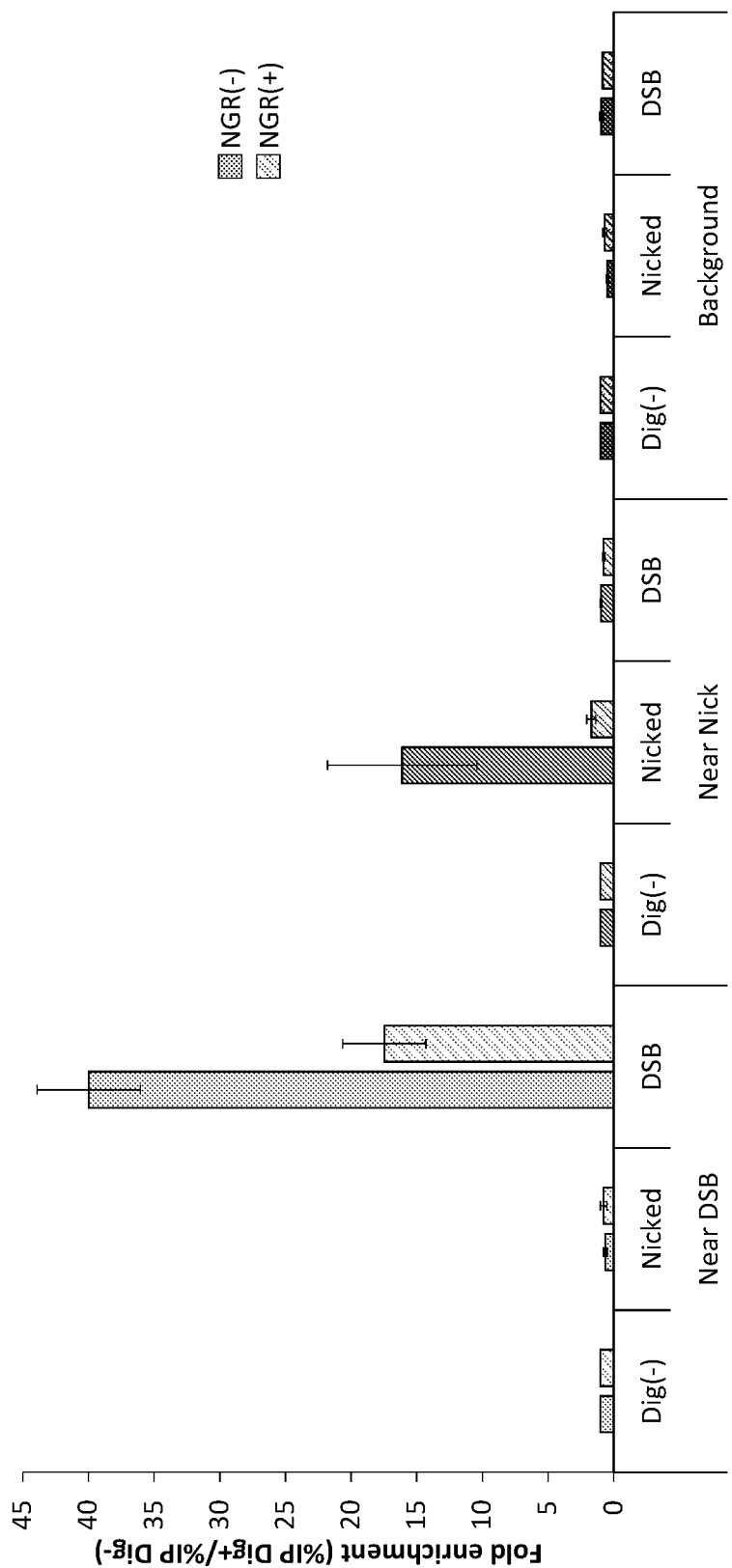
FIG. 1 provides a specific mapping of double-strand break (DSB). Fold enrichment represented as the ratio of % IP compared to undigested control DNA from HeLa-I-SceI cells with (NGR(+)) or without (NGR(−)) NGR. Dig(−), undigested HeLa-I-SceI DNA; Nicked, Nt.BbvCI-digested HeLa-I-SceI DNA; DSB, I-SceI-digested HeLa-I-SceI DNA. Prior to immunocapture, DNA was digested with Taq$^{\alpha}$I. Input and immunocaptured DNA were quantified by qPCR using primer pairs targeting regions shown in FIG. 5C. Error bars represent ±SEM from technical triplicates.

The present disclosure provides a method for quantifying double-strand breaks (DSBs) in deoxyribonucleic acid (DNA) molecules by using a terminal deoxynucleotidyl transferase (TdT) to selectively label the 3'-OH free termini that can be present in a double-strand DNA molecule following a prior step of DNA nick sealing and gap repair. The method can be used on genomic DNA to label and eventually quantify genomic DSBs. In an embodiment, the method can be used to label and eventually quantify each DSBs in one or more of a double-strand DNA molecule. When paired with whole genome sequencing, the method can be used to localize the DSBs to specific loci in the genome. Advantageously, and as shown in the Example below, DSBs occurring due to mechanical shearing are not labeled (and therefore cannot be quantified) by the present method. Furthermore, the methods can be used not only on isolated nuclei but on samples of DNA molecules that have been submitted to mechanical shearing, for example on isolated DNA molecules.

The methods described herein can be used in many fields in which the determination of the presence, the number and/or the position of DSBs may be required. The methods has applications in testing novel chemicals for genotoxicity (including chemotherapy, ionizing radiation for example), monitoring environmental contamination with genotoxins, human biomonitoring, molecular epidemiology as well as fundamental research in DNA damage and repair. When used in human biomonitoring and molecular epidemiology, the method can be specifically applied in cancer as well as in fertility (to determine, amongst other things, the sperm DNA fragmentation level). The methods of the present disclosure can be used to identify and quantify any DNA damage or adduct that can be converted to DSBs by an enzymatic reaction (endogenous or exogenous to the cell). The methods described herein can be used to determine the presence and quantity of DSBs caused by, for example, oxidation, alkylation, hydrolysis, bulky adduct formation, base mismatches, monoadduct damage, diadduct damage as well as those cause by exogenous agents (such as, for example, UV light, ionizing radiation, thermal disruption and exposure to chemicals).

The method can be used on any sample comprising at least one double-strand DNA molecule. The sample can comprise a double-strand DNA molecule, be a synthetic double-strand DNA molecule(s) or a substantially isolated double-strand DNA molecule(s). As used in the context of the present disclosure, a double-strand DNA molecule is considered "substantially isolated" when the majority of cellular components/enzymatic reaction with which it was associated in a cell or reaction mixture are no longer associated with the double-strand DNA molecule. As such the sample can be a biological sample or be derived from a biological sample. As used in the context of the present disclosure, a "biological sample" is a sample of an individual or a plant's fluid, cells or tissues. For example, the biological sample can be derived from a tumor tissue and may even comprise tumor cells. Alternatively or in combination, the biological sample can be derived from the individual's blood and may even comprise blood cells (including cancerous blood cells). The biological sample can be derived from sperm and comprise spermatozoon. The sample can be a microbial sample or be derived from a microbial cell. As used in the context of the present disclosure, a microbial sample can be from a bacteria (or a bacterial infected sample), a yeast or a fungus (or a yeast or a fungal infected sample), a virus (or a virally infected sample) or be derived from a microbial cell. The sample can be used without prior modification in the various methods described herein. Optionally, the biological sample can be treated (mechanically, enzymatically, etc.) prior to the methods described herein for example to substantially isolate the double-strand DNA molecule(s) from the cells.

The methods described herein are especially useful for the quantification of DSBs in DNA molecules suspected of having DNA nicks, DNA gaps and double-strand DNA breaks. As used in the context of the present disclosure, a "DNA nick" is a type of single-strand DNA break resulting in the discontinuity on one strand of a double-stranded DNA molecule, more specifically a lack of a phosphodiester bond between two adjacent nucleotides. A "DNA gap" is another type of single-strand DNA break resulting in a discontinuity on one strand of a double-stranded DNA molecule, however it is a lack of one or more adjacent nucleotides on only one strand of the double-stranded DNA molecule. A "double-strand DNA break" refers to a discontinuity in both strands of double-stranded DNA molecules leading to the division of a DNA molecule in two distinct fragments, more specifically it refers to a damage in which both strands either lack a phosphodiester bond between two adjacent nucleotides or to a lack of one or more adjacent nucleotides on both strands.

The first step in the methods described herein is to proceed to a nick and gap repair step prior to the step of labelling the free 3'-OH termini from DSB only (using a terminal deoxynucleotidyl transferase or TdT). The TdT introduces a label to the free 3'-OH termini which is either used to quantify the DSBs and as such it is important that only the 3'-OH termini are labelled by the TdT. The nick and gap repair step will insure that the DNA nicks (which can be repaired/sealed using a DNA ligase) and the DNA gaps (which can be repaired using a DNA polymerase) that may be present in the double-strand DNA molecule(s) are repaired. This step thus ensures that only the 3'-OH termini from DSB (which cannot be repaired by the DNA ligase or the DNA polymerase) is available for labeling by the terminal deoxynucleotidyl transferase. If this nick and gap repair step is omitted, the terminal deoxynucleotidyl transferase would label not only the 3'-OH free termini of the DSBs, but also the DNA nicks and gaps, which would lead to an incorrect determination of the DSBs. In an embodiment, the nick and gap repair is able to seal the majority and, in some embodiments, the totality of the DNA nicks and gaps that may be present in the double-strand DNA molecule(s).

As indicated above, the step of nick and gap repair requires the use of a DNA ligase to repair the one or more DNA nicks that may be present in the double-strand DNA molecule(s). DNA ligases are specific ligases (EC 6.5.1.1) that facilitate the joining of DNA strands together by catalyzing the formation of a phosphodiester bond. In the context of the present disclosure, the DNA ligase should specifically be capable of repairing single-strand DNA breaks (e.g., nicks) and used under conditions (for example temperature, time of incubation and type of DSBs) in which SSBs are preferably repaired (when compared to DSBs). Ligase activity is usually measured in Weiss unit which refers to the amount of ligase that catalyzes the exchange of 1 nmole of $^{32}P$ from inorganic pyrophosphate to ATP in 20 minutes at 37° C. The DNA ligase that can be used in connection with the method described herein can be a bacterial ligase (such as, for example, an *Escherichia coli* ligase), a viral ligase (such as, for example a T4 DNA ligase), a mammalian ligase (such as, for example, a DNA ligase I, a DNA ligase III and/or a DNA ligase IV) as well as combinations thereof. The DNA ligase can be made from recombinant technology. In an embodiment, the DNA ligase used in the method is a viral DNA ligase, such as, for example the T4 DNA ligase. In another embodiment, the T4 DNA ligase is used in combination with a T4 DNA polymerase in the nick and gap repair step. In still another embodiment, the activity of the T4 DNA ligase per µg of DNA to be repaired is at least about 100U, 200U, 300U, 400U, 500U, 600U or 700U. In yet another embodiment, the activity of the T4 DNA ligase per µg of DNA to be repaired is about 400U.

As also indicated above, the step of nick and gap repair requires the use of a DNA polymerase to repair the one or more DNA gaps that may be present in the double-strand DNA molecule(s). It is important that, at this step, the contact of the DNA polymerase with the sample does not cause the amplification (either by PCR or using NGS) of the DNA molecules and only serves to fill in the DNA gaps that may be present in the DNA molecules. DNA polymerase is a specific polymerase (EC 2.7.7.7) that synthesizes DNA molecules from deoxyribonucleotides. DNA polymerase activity can be measured in unit, defined as the amount of enzyme that will incorporate 10 to 15 nmol of dNTP into an acid insoluble material in 20 to 30 minutes at 55 to 75° C. (depending on the enzyme). DNA polymerases can be classified in families based on sequence homology (A, B, C, D, X, Y and RT) and DNA polymerases from all of these families can be used in the methods described herein. For example, the DNA polymerase that can be used in connection with the method described herein can be a prokaryotic DNA polymerase (Pol I, Pol II, Pol III, Pol IV and/or Pol V), a eukaryotic polymerase (polymerase β, λ, σ, µ, α, δ, ε, η, ι, κ, Rev1, ζ, telomerase and/or ν), a viral polymerase (T4 DNA polymerase) as well as combinations thereof. In an embodiment, the DNA polymerase used in the methods described herein is the T4 DNA polymerase. In another embodiment, the T4 DNA polymerase is used in combination with the T4 DNA ligase in the nick and gap repair step. In still another embodiment, the activity of the T4 DNA polymerase per µg of DNA to be repaired is at least about 0.1U, 0.5U, 0.75U, 1U, 2U, 3U or 4U. In yet another embodiment, the activity of the T4 DNA polymerase per µg of DNA to be repaired is about 1U.

The nick and gap repair step of the method requires the use of two different enzymes which can be used simultaneously or sequentially. For example, the double-strand DNA molecules can be first submitted to the enzymatic activity of the DNA ligase and then to the enzymatic activity of the DNA polymerase. In such example, the double-strand DNA molecules should be submitted further to the enzymatic activity of the DNA ligase, after the step DNA polymerase step, to repair the nicks present after the reparation of gaps by the DNA polymerase. Alternatively, the double-strand DNA molecule can be first submitted to the enzymatic activity of the DNA polymerase and then to the enzymatic activity of the DNA ligase. In yet another example, the double-strand DNA molecule can be submitted to the simultaneous enzymatic activities of the DNA ligase and the DNA polymerase.

Figure 6:
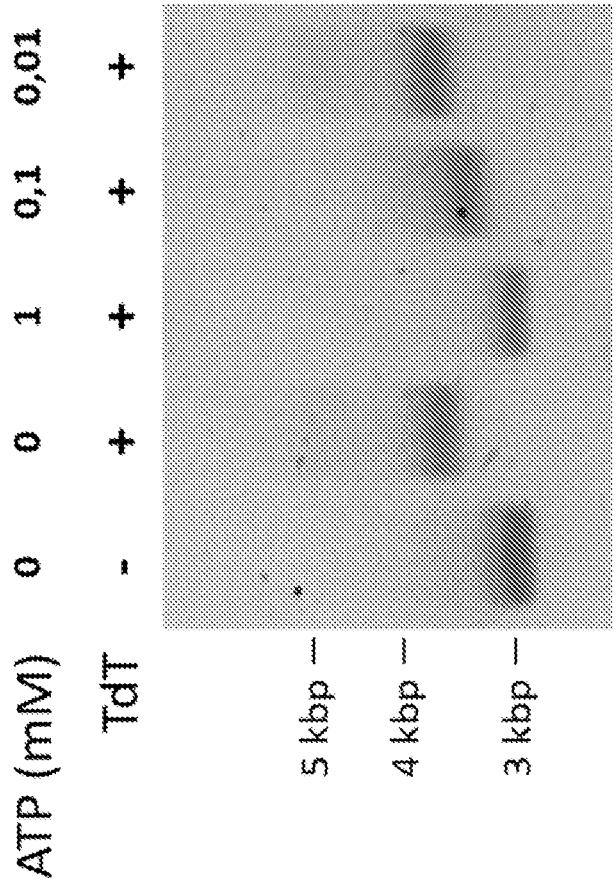
FIG. 6 shows TdT inhibition by ATP. Linearized pBlue-Script plasmid was used in a tailing reaction using TdT and dATP following manufacturer's instruction. Different concentrations of ATP were added in the reaction and the tailing efficiency was observed after agarose gel electrophoresis by a shift in the DNA size.

The nick and gap repair step is conducted in conditions so as to allow the reparation of the majority or totality of the DNA nicks and gaps, to avoid the reparation of the DSBs and/or to inhibit the amplification of the DNA molecules. In order to do so, it may be necessary to select specific buffer(s), reagent(s) and reactions conditions (time and temperature) allowing the DNA ligase and the DNA polymerase to exhibit their enzymatic activity. In one assay format, the enzymatic conditions can be adjusted in order for the DNA ligase and the DNA polymerase to be both enzymatically active at the same temperature and in the same buffer (e.g., in the presence of the same reagents). In another complementary or alternative assay format, the concentration of adenosine triphosphate (e.g., ATP, a reagent used by the DNA ligase, the DNA polymerase and the TdT) can be adjusted so that it does not limit downstream enzymatic activity. For example, as indicated below, it was determined that it is possible to conduct the TdT labeling step directly in the buffer of the nick and gap repair step to limit loss in DNA molecules, gain in efficiency and precision. However, the usual concentration of ATP for DNA ligase and DNA polymerase (10 µM) has been shown to inhibit the enzymatic activity of the TdT (see FIG. 6). As such, in embodiments in which the TdT labeling step is conducted directly after the nick and gap repair step (e.g., the DNA molecules have not been isolated between the two steps), it is necessary to use a concentration of ATP lower than 10 µM, for example, a concentration equal to or lower than 9 µM, 8 µM, 7 µM, 6 µM, 5 µM, 4 µM, 3 µM, 2 µM, 1 µM or lower in the buffer for the enzymatic reactions.

Once the nick and gap repair step is completed, then the sample or the isolated DNA molecules are contacting with a terminal deoxynucleotidyl transferase (TdT) to add nucleotides at the free 3'-OH termini found in the sample. In some embodiment, the labelled nucleotide can be a terminator nucleotide (e.g., a nucleotide which does not allow the addition of a further nucleotide by the TdT). Optionally, non-labeled/non-terminator nucleotides can also be admixed with the TdT and the labeled nucleotides to facilitate or enhance the enzymatic activity of the TdT. In an embodiment, the majority of the DSBs are labeled by the TdT and, in still another embodiment, all the DSBs are labeled by the TdT. As indicated above, it is not necessary (and may even be preferable not) to isolate the DNA molecules which have been submitted to nick and gap repair prior to the labeling step with the TdT. The DNA molecules that have been submitted to the nick and gap repair step can be (directly) submitted to the enzymatic activity of the TdT.

The label associated to the 3'-OH free termini can be used as a detectable label (to quantify directly the presence, number and/or location of the DSBs) and/or as an affinity label (to purify the labeled DNA molecules and eventually quantify the presence, number and/or location of the DSBs). Examples of detectable labels include enzymes, prosthetic groups, fluorescent materials, luminescent materials, bioluminescent materials and radioactive materials. The label can be a radioactive label, which can include, for example, one or more of the following radioisotope $^{125}$I, $^{131}$I, $^{35}$S, $^{32}$P or $^3$H. The label can be an enzyme, for example, one or more of the following horseradish peroxidase, alkaline phosphatase, beta-galactosidase, or acetylcholinesterase. The label can be a prosthetic group, for example, a biotin group which can complex with streptavidin and avidin/biotin. The label can be a light-emitting entity such as a fluorescent label, a luminescent label and/or a bioluminescent label. The label can be a fluorescent label, for example, one of the following umbelliferone, fluorescein, fluorescein isothiocyanate, rhodamine, dichlorotriazinylamine fluorescein, dansyl chloride or phycoerythrin. The label can be a luminescent label which can be, for example, luminol. The label can be a bioluminescent label, such as, for example a luciferase, luciferin and/or aequorin.

In some embodiments (for example in fundamental research), it is necessary to modify the isolated DNA molecules with the TdT prior to the nick and gap repair, to block endogenous DNA breaks. In such embodiments, the modified DNA molecules are then submitted to potentially damaging conditions (irradiation and/or apoptosis for example)

which can potentially induce novel (unblocked) DSBs. These new DSBs can be identified by submitting the modified DNA molecules to nick and gap repair and TdT treatment as described herein. As such, the optional preliminary TdT treatment can allow to specifically determine damages caused to the genetic material caused by the specific and potentially damaging conditions such as, for example, irradiation and/or apoptosis.

The terminal deoxynucleotidyl transferase (TdT) is a specialized DNA polymerase that can enzymatically add a nucleotide to the 3'-OH free termini (E.C. 2.7.7.31). TdTs do not require a template to make such addition. Any type of TdT can be used in the methods described herein. For example, the TdT can be derived from human (Gene ID 1791), mouse (Gene ID 21673), rat (Gene ID 294051), cow or any other eukaryotic source. The TdT can be provided from recombinant technology. In still another embodiment, the activity of the TdT ligase per µg of DNA to be labelled is at least about 100U, 200U, 300U, 400U, 500U, 600U or 700U. In yet another embodiment, the activity of the TdT per µg of DNA to be labelled is about 500U. In some embodiments, it may be preferable to inactivate the TdT (for example by used heat) prior to conducting downstream steps.

Once the labeling step with TdT is completed, a purification step is conducted to remove the unreacted nucleotides which may interfere with the downstream steps of the method. For example, the purification can be made by selecting the unreacted nucleotide from the enzymatic mixture. Alternatively, the purification can be made by selecting the labeled DNA molecule(s) from the enzymatic mixture. This can be done, for example, using a solid support either capable of selectively binding DNA molecules (such as, for example a silanol-based support) or to the label of the DNA molecules (such as, for example, using streptavidin, avidin and/or an antibody specific for the label). Such solid support can be a column or a bead (a magnetic bead for example) which can be washed (to remove the unreacted nucleotides) and from which the DNA molecules can be eluted. Alternatively, the purification step can include a salt precipitation step to precipitate the DNA molecules out of the enzymatic mixture. To facilitate the binding, capture, precipitation and/or elution of the DNA molecules and prior to these steps, it may be advisable to include a fragmenting step to reduce the length of the DNA molecules. Enzymes that can be used to this end include, but are not limited to $Taq^{\alpha1}$, a double-strand DNA Shearase™ and/or a Fragmentase®. Also, the purification step can include an electrophoretic purification to select DNA molecules having a specific size or range. Once the purification has been completed, the DNA molecules are referred to as being substantially isolated since they are been dissociated from the majority of the components of the enzymatic mixture.

The method can optionally provide an amplification step, an arraying step and/or a sequencing step of the substantially isolated DNA molecules. This optional step can be performed to provide information about one or more specifically localized DSB (using amplification or an array (such as, for example, a micro-array) or to map the locations of the DSBs in the genome (using arraying or sequencing, especially next generation sequencing). When amplification, array or sequencing steps are performed in the method, it may be advisable to include a fragmenting step to reduce the length of the DNA submitted to amplification, array or sequencing. Enzymes that can be used to this end include, but are not limited to $Taq^{\alpha1}$, a double-strand DNA Shearase™ and/or a Fragmentase®.

In order to provide a quantification of the DSBs in the sample, the method provides a step of quantifying a signal either associated with the labeled DNA molecules (obtained after the enzymatic treatment with TdT), associated with the amplification the DNA molecules and/or associated with the sequence of the DNA molecules. For example, when the label is a radioisotope, the method provides quantifying the radioactivity associated with the DNA molecules to quantity the DSBs in the sample. In yet another example, when the label is an enzyme capable of metabolizing a substrate to provide a color, the method provides quantifying the color associated with the DNA molecules to quantify the DSBs. In still another example, when the label is biotin and the DNA molecules has been amplified and/or sequenced, the method provides determining the signal associated with the amplification and/or sequence of the DNA molecules to quantify, and optionally map, the DSBs.

The method can optionally include a step of isolating the DNA molecules from the sample prior to the nick and gap repair step. As indicated below, the method is insensitive to DSBs that can be caused during mechanical manipulation of the DNA. As such, the bias that could be introduced by the mechanical manipulation of DNA is avoided in the method presented herein. The method can also optionally include a step of fixing the DNA molecules to a solid support prior to conducting the method to reduce, for example, loss of nucleic material during manipulations and/or facilitate high-throughput processing.

The present disclosure also provides a kit for conducting the method described herein. For example, the kit can comprise one or more of a DNA ligase; a DNA polymerase; a terminal deoxynucleotidyl transferase (TdT); a substrate for the TdT, the substrate comprising a nucleotide having a label; and/or instructions to perform the steps defined herein. Optionally the kit can also include a single buffer for conducting the nick and gap repair step and/or ATP at a concentration lower than 10 µM.

The present invention will be more readily understood by referring to the following examples which are given to illustrate the invention rather than to limit its scope.

Example I—Quantification Using dATP [$\gamma$-$^{32}$P]

Reagents.

For the generation of the HeLa-I-SceI cell lines: SB-I-SceI-3L1 and pCMV(CAT)T7-SB plasmids (FIG. 5) were kindly provided by Dr. Astrid Roy-Engel (Tulane University). PBlueScript 11 SK (+) was purchased from Stratagene (Agilent, USA). Gene-Cellin (#GC1000) was from BioCell-Challenge (Bulldog Bio Inc., USA) and HeLa cells from the ATCC (USA). Blasticidin (#R210-01) was from Invitrogen (Thermo Fisher Scientific, USA). For DNA purification in qTUNEL assays and DNA extractions: Lysis Buffer, Blood (#MD1392) and Alcohol Wash, Blood (#MD1412) were purchased from Promega (USA). Dynabeads® MyOne™ Silane (#37002D) and DynaMag™-2 Magnet (#12321D) were purchased from Invitrogen (Thermo Fisher Scientific, USA). Proteinase K (#BP1700-500) was purchased from Fisher Scientific (Thermo Fisher Scientific, USA). All DNA quantifications were done using Qubit® 2.0 Fluorometer (Thermo Fisher Scientific, Invitrogen, USA) with the QuantiFluor® dsDNA System (Promega, USA). For DBrIC: DNA labeling was performed using TdT (#3333574001) from Roche (Sigma-Aldrich Canada, Roche, Canada) and Biotin-14-dATP (#19524016) from Invitrogen (Thermo Fisher Scientific, USA). β-Agarase 1 (#M0392) and Taq,I (#R0149) were obtained from New England Biolabs (USA).

dsDNA Shearase™ Plus (#E2018-50) was from Zymo Research (USA). For immunocapture, Protein A/G Magnetic Beads (#B23202) were purchased from Bimake (USA) and anti-Biotin antibody (#ab6643) was from Abcam Inc. (USA). For qTUNEL labeling: dATP, [γ-$^{32}$P]-3000 Ci/mmol (#BLU012H500UC) was obtained from PerkinElmer (USA) and ddATP was from Roche (Sigma-Aldrich Canada, Canada). DNA fragmentation was performed using NEBNext® dsDNA Fragmentase® from New England Biolabs (USA). Radioactive quantification was performed using EcoLite(+)™ Liquid Scintillation Cocktail (MP Biomedicals, USA) and Beckman LS 6500 Scintillation System (Beckman Coulter, USA). For single-strand break repair, T4 DNA ligase (#M0202), T4 DNA polymerase (#M0203) and NEBuffer 2.1 (#67202) were purchased from New England Biolabs (USA). For deep-sequencing: SPARK™ DNA Sample Prep Kit for Illumine® (#SPK0001-V08) was purchased from Enzymatics (D-MARK Biosciences, Canada).

Construction of the HeLa-l-SceI Model.

Figure 5B:
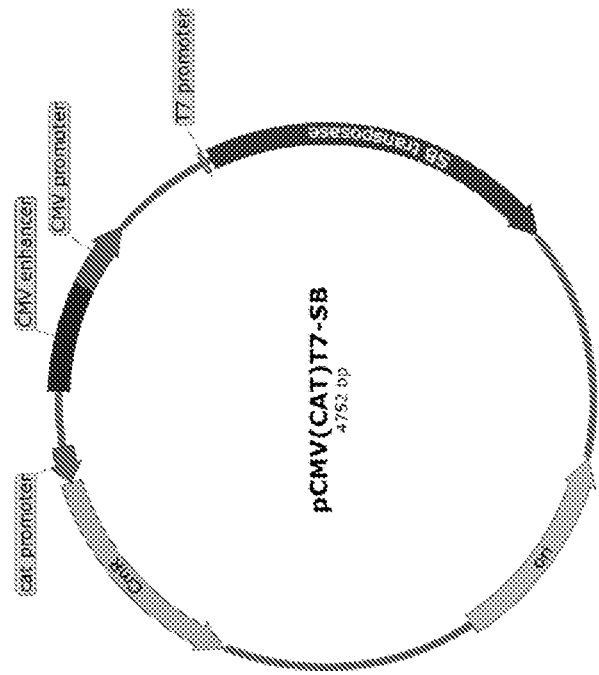
FIG. 5B shows the pCMV(CAT)T7-SB plasmid.
Figure 5A:
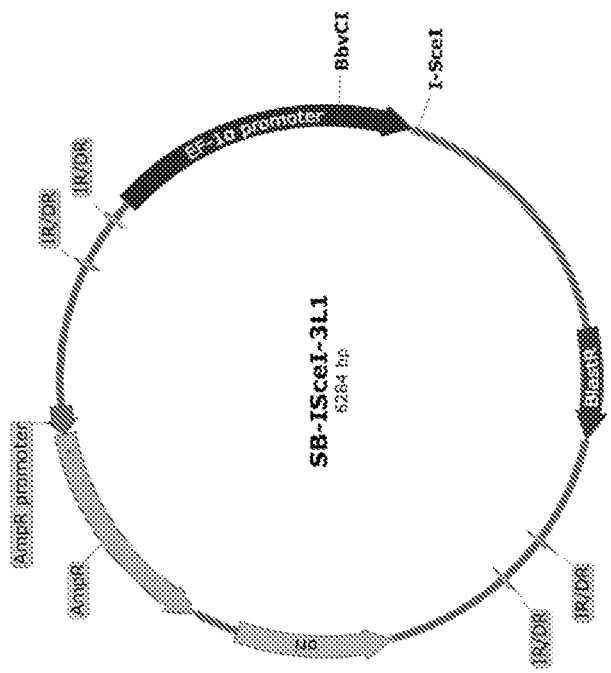
FIG. 5A shows the SB-I-SceI-3L1 plasmid.

SB-I-SceI-3L1 is a pUC57 plasmid containing a cassette harboring the I-SceI recognition sequence and the blasticidin resistance gene under the human elongation factor-1 alpha promoter. The cassette is flanked by Inverted Repeats/Direct Repeats (IR/DR) used by the Sleeping beauty transposase for insertion of the transposon (FIG. 5A). pCMV(CAT)T7-SB plasmid contains the Sleeping beauty transposase under the control of the human cytomegalovirus promoter (FIG. 5B). Both plasmids were stably transfected into HeLa cells using Genecellin and pBlueScript II SK (+) as carrier, according to manufacturer's instructions. Following selection with blasticidin for one week, cells were trypsinated and plated in 96 well plates using a BD FACSAria™ III cell sorter to individualize the cells and start a clonal cell line harboring the incorporated insert. Clonal cell lines were maintained under blasticidin selection. Incorporation was assessed by qPCR using primers targeting on the insert.

DNA Extraction.

Ten million HeLa-I-SceI cells were trypsinated, washed once with 1×PBS and lysed for 4 h at 55° C. in 500 μL of 2.5 M NaCl, 100 mM EDTA, 10 mM Tris-HCl; pH 8.0, supplemented with 1% Triton X-100, 0.2 mg/ml proteinase K, 10 mM DTT and 0.1 mg/ml RNase A just before use. Five hundred microliters of Lysis Buffer (Promega) was added, followed by 200 μL of Dynabeads® MyOne™ Silane and 500 μL of 100% isopropyl alcohol. DNA was allowed to bind to the magnetic beads for 5 min by rotation at room temperature. DNA bound to the beads was washed once using 1 mL of Lysis Buffer using the magnet and twice with 1 mL of Alcohol Wash. The DNA bead pellet was allowed to dry for 5 min at room temperature. DNA was eluted with 500 μL of elution buffer (10 mM Tris-HCl; pH 9.0, 0.1 mM EDTA) pre-warmed at 65° C.

DNA Digestions and Fragmentations.

DNA digestion methods where as outlined in legend to figures. For FastPrep mechanical fragmentation, 0.5 mm glass beads were added to 100 μL genomic DNA and fragmented for 1 min at 6 500 RPM. For sonication, DNA was fragmented using a Misonix sonicator S-4000 for 6×30 s at amplitude 25, with 10 s lapse between each pulse. I-SceI and Nt.BbvCI were used to create a unique DSB and to nick the DNA, respectively, with 3 U per μg DNA for 4 h at 37° C. followed by heat inactivation for 20 min at 80° C. DNA for qTUNEL was digested with 0.5 U of dsDNA Shearase per μg DNA for 20 min at 42° C. and heat inactivated for 5 min at 65° C.

Nick and Gap Repair.

DNA nick and gap repair (NGR) was performed in two steps at a final concentration of 40 ng/μL DNA, 1×NEBuffer 2.1, 0.1 mM dNTP, 1 μM ATP and 400 U T4 DNA ligase per μg DNA. Nick sealing was allowed to proceed for 10 min at 12° C. and one unit of T4 DNA polymerase per μg DNA was added to fill the remaining gaps for 15 min at 12° C. Reactions were terminated by heat inactivation for 20 min at 75° C. Subsequent labeling reactions for either DBrIC or qTUNEL were performed directly, without any prior DNA purification step.

DNA Break Immunocapture.

Three prime hydroxyl DNA ends were labeled for 15 min at 37° C. at a final concentration of 20 ng/μL DNA, 1×TdT reaction buffer, 5 mM CoCl$_2$, 0.1 mM dATP, 6.25 μM Biotin-14-dATP and 500 U of TdT per μg DNA. TdT was heat-inactivated for 10 min at 65° C. Labeled DNA was purified with either ethanol precipitation or embedded in agarose plugs, followed by 3×20 min washes in 1×TE on a rotating wheel. Plugs were then digested with β-Agarase in 1×TE buffer. Plug washes have the advantage of limiting unincorporated nucleotide carryover and DNA loss through ethanol precipitation. Purified labeled DNA was fragmented with either Taq$^{αI}$ (66.7 U per μg DNA) or dsDNA Shearase (1.75 U per μg DNA) in appropriate buffer. Immunoprecipitation was carried out following the manufacturer's protocol with minor modifications. Thirty microliters of Protein NG Magnetic Beads and 1.2 μg of anti-Biotin antibody per μg of starting DNA were used in 2 to 4 vols of the initial beads. Antigens were allowed to bind antibodies on beads for 1 h at room temperature on a rotating wheel in 1×IP buffer (1×PBS, 0.02% Tween-20). Four washes were performed in 1×IP buffer using the magnet and immunocaptured DNA was eluted in one initial bead volume of ultrapure water at 80° C. for 20 min using a thermomixer.

qTUNEL.

Radioactive labeling for qTUNEL was performed for 15 min at 37° C. with 200 ng DNA, 1×TdT reaction buffer, 5 mM CoCl$_2$, 0.1332 mM dATP, [γ-$^{32}$P], 0.01332 μM ddATP and 400 U TdT in a final volume of 25 μL. Labeling reaction was stopped by heat inactivation for 15 min at 65° C. An optional fragmentation step can be added for high molecular weight DNA to facilitate DNA binding on the beads and elution in the subsequent steps by adding 0.5 U of Fragmentase® and 4.5 μL of water and incubating for 20 min at 37° C. Enzymatic reactions were stopped while recovering the labeled DNA by adding 40 μL Lysis Buffer, 10 μL water, 10 μL Dynabeads® MyOne™ Silane and 40 μL 100% isopropyl alcohol. DNA was allowed to bind to the beads for 8 min on a rotating wheel at room temperature. Using the magnet, DNA was washed once with 700 μL of Lysis Buffer and once with 700 μL of Alcohol Wash. The DNA-bead pellet was dried for 5 min at room temperature and eluted for 15 min with 40 μL of elution buffer (10 mM Tris-HCl; pH 9.0, 0.1 mM EDTA) prewarmed at 65° C. Ten microliters of radiolabeled DNA was quantified in triplicate using Qubit® fluorometer. The same tubes used to quantify DNA were opened, inserted in scintillation vials with 5 mL of Scintillation Cocktail and quantified using scintillation counter.

Next-Generation Sequencing.

DNA extracted from HeLa-I-SceI cells was either nicked by Nt.BbvCI or digested with I-SceI, while undigested DNA was used as control. Each preparation underwent NGR or left unrepaired. DBrIC was performed with 1 μg of starting DNA and sequencing libraries were generated from immunocaptured fragments by ligating custom adapters for Illumine paired-end sequencing containing 6 bp barcodes as previously described [Rodrigue et al., 2010], but using the SPARK™ DNA Sample Prep Kit for Illumina® according to the manufacturer's instruction. Quality control was performed by analyzing the size distribution and concentration of libraries using an Agilent 2100 Bioanalyzer high-sensitivity DNA chip. Libraries were mixed in defined ratios and sent to sequencing at the Institut de Recherches Clinique de Montréal resulting in approximately 220 million 50 bp paired-end reads from a single HiSeq 2000 lane. Mapping was done using our in-house Galaxy-GenAP platform against the insert sequence using BWA [Li et al., 2009] and PCR duplicates were removed using Picard [Broad Institute 2016]. Reads were visualized with Tablet software [Milne et al., 2013]. 3.1. Specific determination and mapping of double-strand breaks Specific Determination and Mapping of Double-Strand Breaks.

Figure 5C:
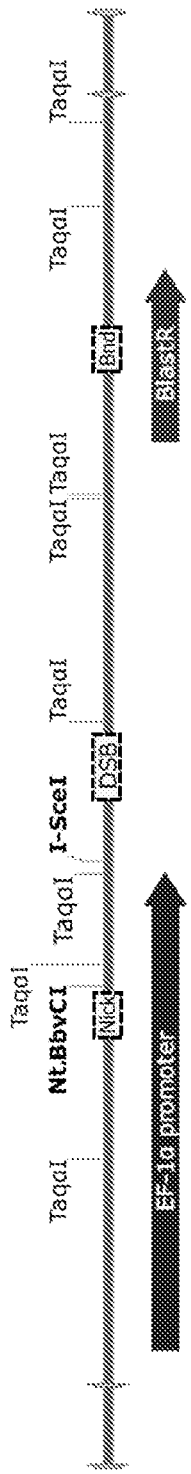
FIG. 5C shows the insert stably transfected into HeLa cells. Grey arrows, Inverted repeats/Direct repeats (IR/DR) used by Sleeping beauty transposase to insert the transposon; Black arrow, Human elongation factor-1 alpha promoter; BlastR arrow, Blasticidin resistance gene; Dotted segments, qPCR amplicon regions used to quantify the immunocaptured fragments; Nick, near nick created by Nt.BbvCI; DSB, near DSB created by I-SceI and Bnd, Background. Taq$\alpha$I, Nt.BbvCI and I-SceI are restriction sites. Maps were created with SnapGene® software Version 3.4.1 (from GSL Biotech; available at snapgene.com).

It was sought to determine conditions for efficient repair of DNA nicks and gaps prior to the TdT end labeling. A proper combination of T4 DNA ligase and T4 DNA polymerase was used to seal nicks and fill the gaps respectively and termed «Nick and Gap Repair» (NGR). The NGR first step is facilitated since T4 DNA ligase was found to be active in the buffer used for T4 DNA polymerase and because both enzymes can be used at the same temperature. Limiting the purification steps is crucial to improve DNA recovery throughout the process. It was observed that TdT is inhibited by the high concentration of ATP recommended for DNA ligations (1 mM, FIG. 6). However, it was determined that efficient DNA nick sealing is still observed by decreasing the ATP concentration to 1 µM. That much lower concentration of ATP now allows the subsequent TdT reaction to proceed normally. From these simple modifications, both repair and labeling reactions can be performed without the need for DNA purification between these steps. It is worth noting that although the use of «Tap» DNA ligase would have the advantage of preventing DSB ligations, T4 DNA ligase was however strongly preferred because of its compatibility with the gap-filling step and its greater nick sealing activity (not shown). The efficiency of the repair step for the specific capture of DSBs within genomic DNA was established using HeLa-I-SceI DNA pre-digested with the nicking endonuclease Nt.BbvCI as this enzyme creates a single nick within a 7 nucleotide recognition sequence. A single Nt.BbvCI recognition sequence is present within the I-SceI insert and can be detected by DBrIC using a primer pair adjacent to the nick (FIG. 5C).

As shown in FIG. 1, the enzyme-induced nick results in a sharp increase in the capture of the sequence ("Near Nick" bars) compared to the undigested control DNA and shows a 15-fold increase in the % IP. Repair of the nicked DNA by NGR restored the % IP to the undigested control (background) level demonstrating that the repair reaction completely eliminates individual nicks and thus proceeds efficiently when mammalian genomic DNA is used as substrate.

Although NGR eliminates most of the DNA nicks and leaves DSBs, its impact on existing DSBs was investigated. As shown in FIG. 1, induction of a DSB by I-SceI digestion of HeLa-I-SceI genomic DNA generates a strong immunocapture at this site ("Near DSB" bars). NGR was however found to decrease the number of immunocaptured fragments around this site to 50%. This was not surprising since I-SceI digestion produces a 4-nucleotides 3'-protruding cohesive end with a high propensity for self-ligation by T4 DNA ligase. Clear detection of this site is nevertheless observed despite this reduction in capture as a result of NGR. Naturally-occurring DSBs, however, have heterologous DNA ends that should minimize ligation by the NGR step. Thus, NGR efficiently eliminates DNA nicks and gaps allowing specific labeling and capture of DSBs.

Mechanical DNA Breaks are not Labeled by TdT.

Figure 2A:
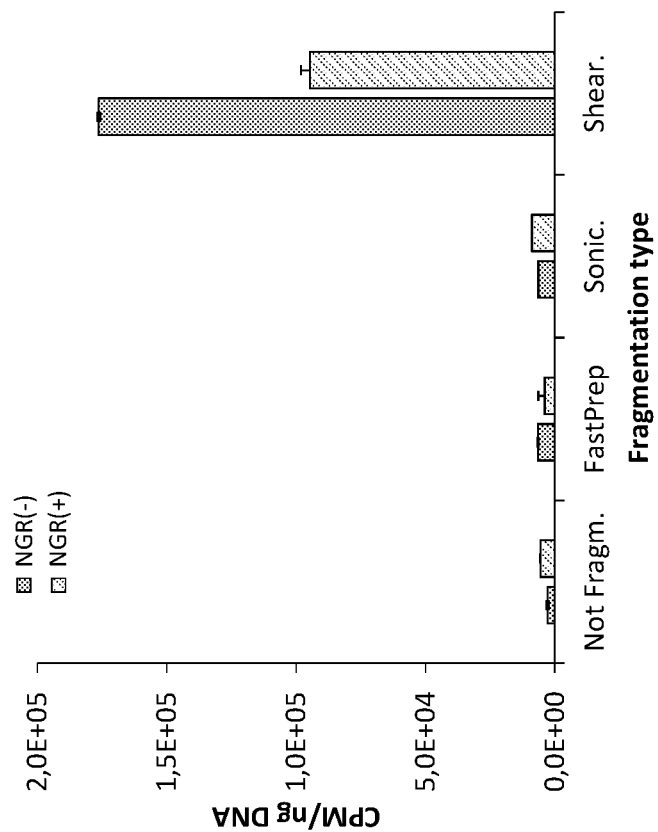
FIG. 2A illustrates a neutral agarose gel electrophoresis showing DNA size fractionation without (−) and with (+) NGR using different shearing techniques.
Figure 2B:
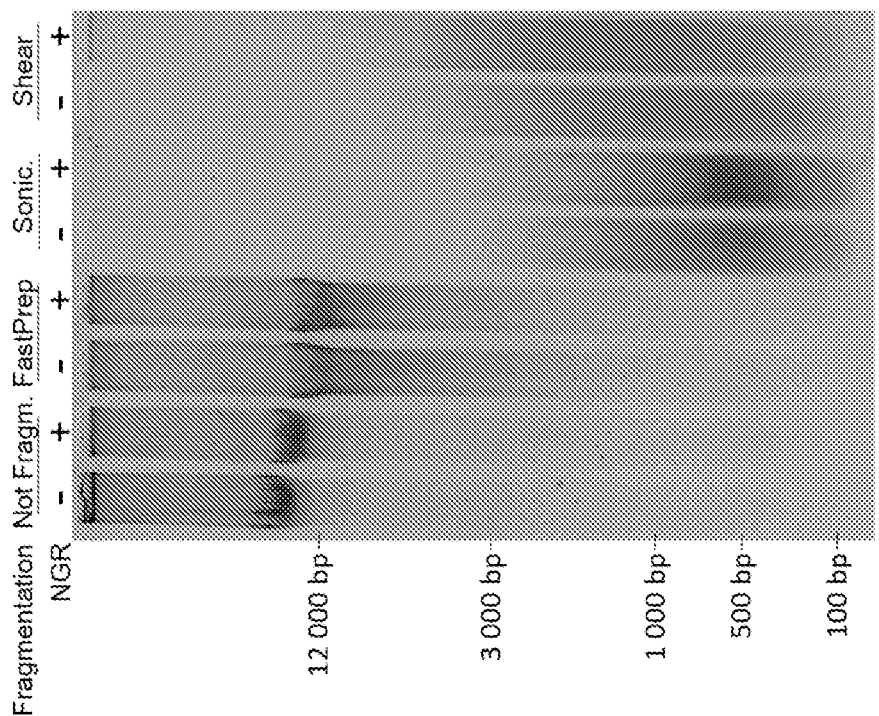
FIG. 2B shows the determination of 3'-OH DNA ends (as represented by CPM per ng DNA) with unrepaired (NGR (−)) and repaired (NGR(+)) DNA after mechanical or enzymatic shearing. Not Fragm., Intact genomic DNA; FastPrep, FastPrep fragmented DNA; Sonic., Sonicated DNA; Shear., dsDNA Shearase-digested DNA. Error bars represent ±SEM from technical triplicates.

Many investigations on DNA strand breaks rely on cell lysis within agarose plugs or direct in situ labeling on isolated nuclei to prevent mechanical DNA breaks. Whether mechanical shearing produces 3'-OH DNA ends was therefore investigated using radioactive end-labeling providing a global quantification of the extent of enzymatic DNA strand breakage that was termed «quantitative TUNEL» (qTUNEL). Using qTUNEL, labeling of intact DNA was compared to mechanically sheared DNA (FastPrep) or sonicated DNA. As shown in FIG. 2A, sonicated DNA displays a similar number of DSBs than dsDNA Shearase-digested DNA based on electrophoretic mobility in neutral conditions. However, it was observed that TdT is unable to catalyze the addition of nucleotides for both types of mechanical breaks over the background level in contrast to the sharp increase in labeling observed following the enzymatic action of dsDNA Shearase, used here as positive control (FIG. 2B).

Very few 3'-OH ends were therefore created during mechanical shearing. Importantly, it was showed that the NGR step does not convert mechanical DNA breaks into 3'-OH DNA ends (Compare NGR(-) and NGR(+) in FIG. 2B). These results demonstrate for the first time that both immunocapture and qTUNEL can safely be performed using extracted DNA rather than cells lysed in agarose plugs and will be highly specific for 3'-OH DNA ends generated from enzymatic activities. This represents a significant advantage since enzymatic reactions performed in agarose plugs are less efficient and require longer incubation times leading to important DNA loss by diffusion. In the conditions tested, as low as 200 ng and 1 µg of extracted DNA from any source can be used for immunocapture followed by qPCR and NGS, respectively, whereas only 200 ng of extracted DNA is sufficient for qTUNEL determination.

Sensitivity of the Double-Strand Break Determinations.

Figure 3B:
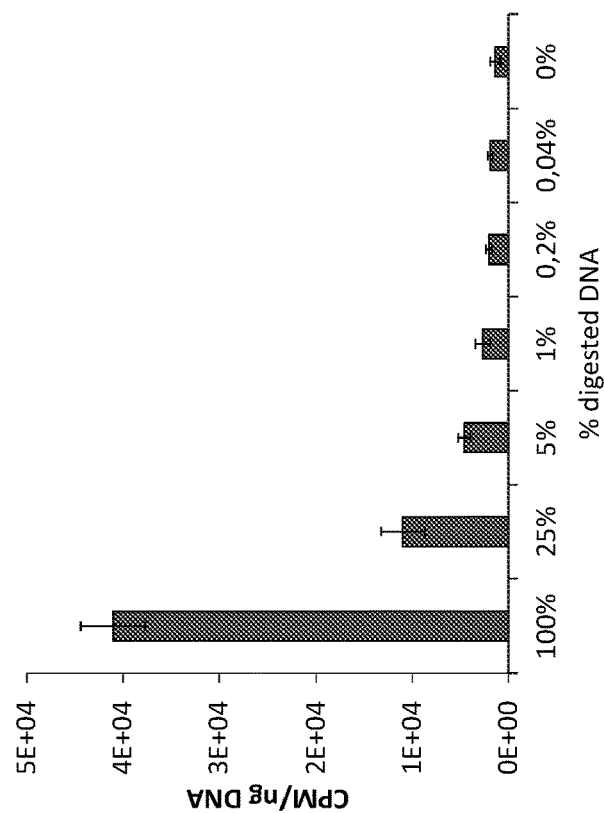
FIG. 3B provides the CPM per ng DNA after qTUNEL using dsDNA shearase-digested DNA mixed with undigested DNA in different ratios. Error bars represent ±SEM from technical triplicates.
Figure 3A:
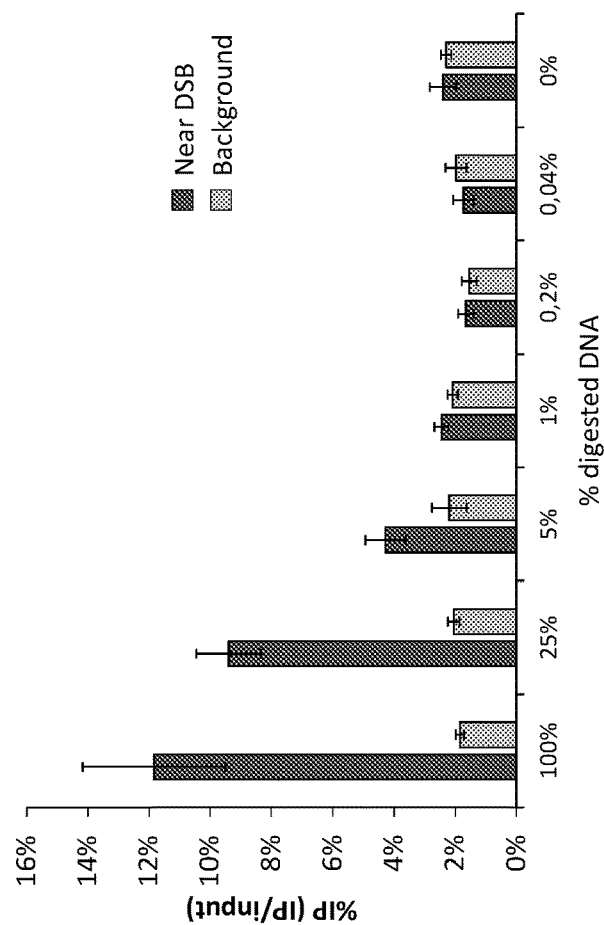
FIG. 3A shows the % IP using I-SceI-digested HeLa-I-SceI DNA mixed with undigested HeLa-I-SceI DNA at indicated ratios visualized by qPCR on immunocaptured DNA using primer pairs either in the vicinity of I-SceI DSB (Near DSB) or within a background region located 883 bp away (FIG. 5C). DNA was fragmented by Taq$\alpha$I prior to immunocapture.

Sensitivity of DBrIC and qTUNEL was established by using different ratios of digested DNA combined to undigested DNA as the input material in order to mimic different levels of fragmentation. For the genome-wide immunocapture, the HeLa-I-SceI model was used to create a unique DSB. In order to establish qTUNEL sensitivity, DNA was instead digested with dsDNA Shearase. As depicted in FIG. 3, both labeling methods can detect as low as 5% variation in DSBs formation either at a defined locus (DBrIC) or globally (qTUNEL).

While detection of 1% digested DNA is not significant when compared to undigested DNA for both methods, it is nevertheless above the background. Interestingly, omission of TdT in the reaction mixture for DBrIC resulted in only 0.05% immunocapture of the input DNA, suggesting that the 2% background capture across samples represents natural endogenous DSBs occurring within the insert. It is worth noting that, given the high level of sensitivity achieved by radioactive labeling, proper qTUNEL determination requires stringent washing steps as described above.

Demonstration of Nick and Gap Repair by Next-Generation Sequencing.

Figure 4:
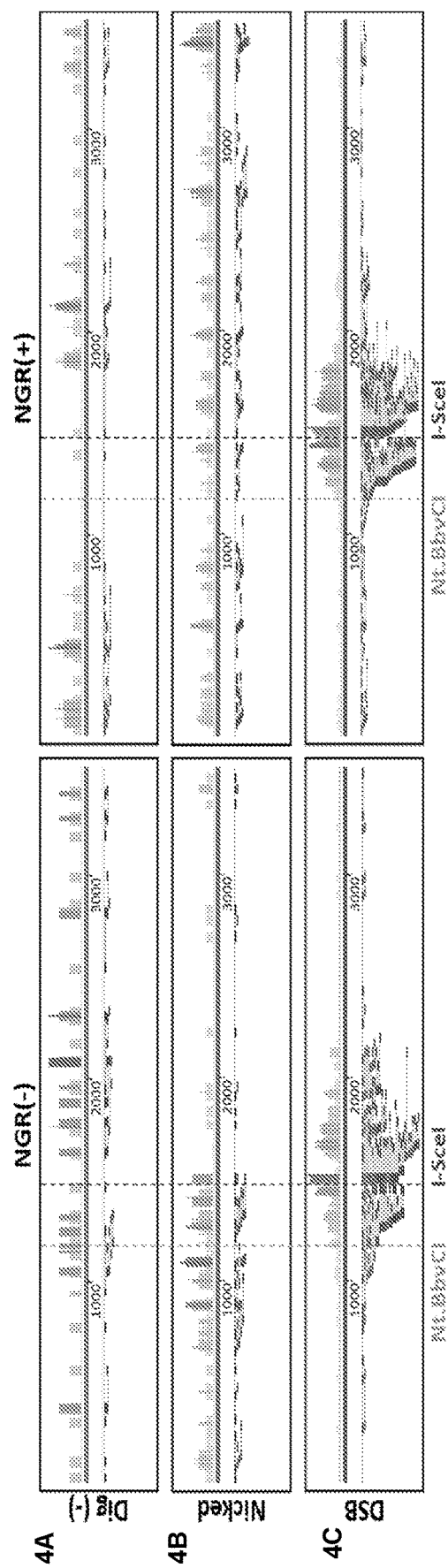
FIG. 4 show a mapping of sequencing reads against I-SceI insert sequence from captured DNA after DBrIC-seq. NGR (−), unrepaired DNA prior to DBrIC (left panels); NGR(+), repaired DNA prior to DBrIC (right panels).

Finally, it was tested whether the immunocapture produced enough output to be used in NGS and to confirm that specificity for DSB is observable on a genome-wide scale. HeLa-I-SceI DNA was used to perform NGR using undigested, nicked and I-SceI digested DNA before DBrIC and Illumine sequencing as described above. The undigested DNA, submitted to NGR or not, produced a few background (endogenous) reads on the insert around the restriction sites of interest (FIG. 4A). When nicked DNA is used as input, increase in sequence reads within the region flanking the nick were now observed. When NGR is performed prior to labeling and immunocapture, reads are no longer observed around the nick (FIG. 4B, Compare NGR(-) and NGR(+)). Finally, the immunocapture also confirms that the I-SceI DSB can be mapped by NGS as reads stack up on both sides of this restriction site either with or without NGR (FIG. 4C, Compare NGR(-) and NGR(+)). Hence, specificity of NGR for SSBs is again demonstrated by NGS confirming that genome-wide mapping of DSBs can be achieved using this simple robust scheme.

This approach represents significant improvements over available mapping and quantification techniques. DSB mapping strategy based on the blunt-ended ligation of a biotinylated adaptor following end repair has been recently published [Crosetto et al., 2011]. While this technique is relatively simple, it has some important limitations. Since the ligation is performed on blunt ended DNA, the absence of stably annealed protruding ends reduces the ligation efficiency of adaptors so a number of DSBs could be missed. In addition, since the ligation step is performed overnight, blunt ended genomic DNA can self-ligate, leading to the loss of DSB loci. Using TdT, as shown in the present example, does not require modification of DNA ends and can label any naturally-occurring 3'-OH ended DNA substrate. In addition, the adaptor ligation technique requires 5 million isolated nuclei which may be difficult to obtain in certain experimental conditions. The strategy described in this paper offers a greater versatility as it can also be used for the determination of any type of strand-breaks if the NGR step is omitted.

One important consideration is that both DBrIC and qTUNEL can be used to study various types of DNA damage, provided that they can be converted into 3'-OH. This requires an initial blocking step with TdT using a terminator nucleotide prior to the enzymatic conversion of the damage. This variation was recently successfully applied by converting UV-induced DNA lesions into 3'-OH by the ultraviolet damage endonuclease (UVDE) [Peyresaubes et al., 2015].

Finally, absolute quantitation of DSBs can be obtained by using a radiolabeled terminator nucleotide such as Cordycepin 5'-triphosphate, [γ-$^{32}$P] to add a single radiolabeled nucleotide. The absolute number of 3'-OH DNA termini is obtained following precise DNA quantification, once specific incorporation is converted from CPM to added terminator molecules. This straightforward NGR approach, combined with TdT labeling, allows to either map or quantify DSBs with specificity and precision not previously achieved. This should allow for an improved monitoring of DNA damage and repair and to explore the impact of different cellular or environmental conditions on genome stability.

Example II—Colorimetric Assay

Figure 7:
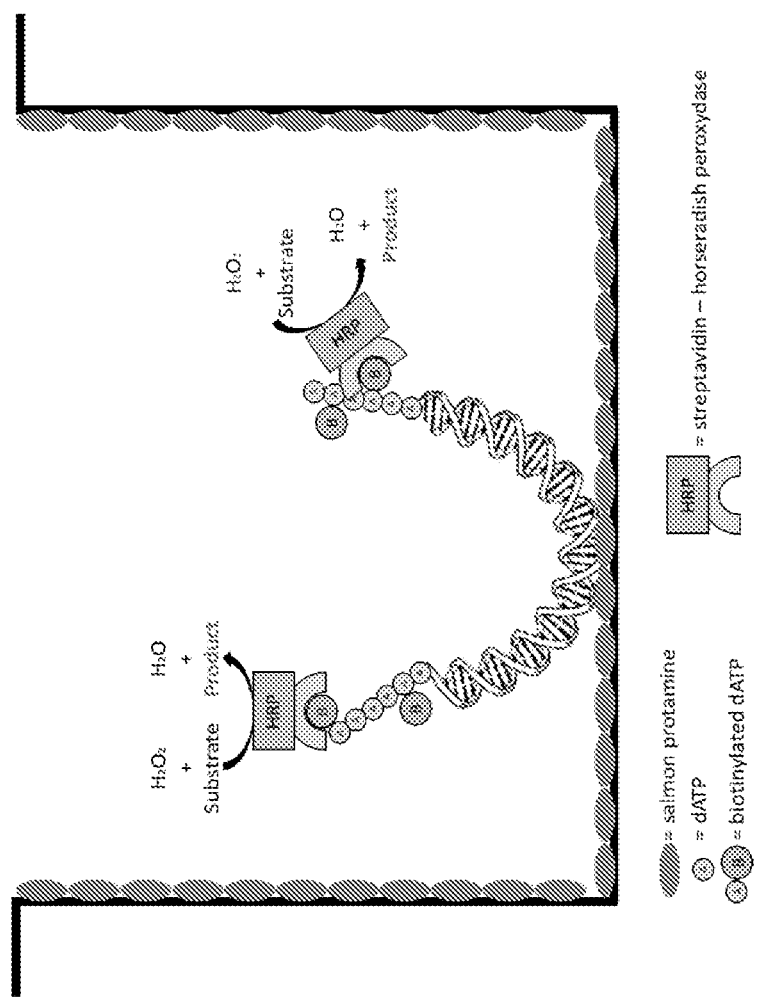
FIG. 7 show an embodiment of the method of the disclosure using a colorimetric detection format.

For convenience and technology transfer to the clinic, the method described in Example I was adapted as a colorimetric assay whereby the DNA to be labeled was immobilized onto protamine-coated microplate wells (see FIG. 7). Following a prior step of nick sealing and gap repair, TdT end-labeling of 3'-OH was performed using biotinylated dATP. The biotinylated ends were then revealed by binding to streptavidin linked to horseradish peroxidase (see FIG. 7). Reaction against the o-phenylenediamine dihydrochloride (OPD) substrate in the presence of $H_2O_2$ produced a yellow color proportional to the amount of DSBs present in the DNA sample. Optical density was determined using a microplate reader and the extent of DSB was established against a standard curve generated by adding know amount of DSB ends from digested recombinant DNA.

While the invention has been described in connection with specific embodiments thereof, it will be understood that the scope of the claims should not be limited by the preferred embodiments set forth in the examples, but should be given the broadest interpretation consistent with the description as a whole.

REFERENCES

A. G. Basnakian, J. S. James, Quantification of 3'-OH DNA breaks by random oligonucleotide-primed synthesis (ROPS) assay, DNA Cell Biol. 15 (1996) 255-262.
N. Crosetto et al., Nucleotide-resolution DNA double-strand break mapping by next-generation sequencing, Nat. Methods 10 (2013) 361-365.
S. Rodrigue et al., Unlocking short read sequencing for metagenomics, PLoS One 5 (2010) e11840.
H. Li, R. Durbin, Fast and accurate short read alignment with Burrows-Wheeler transform, Bioinformatics 25 (2009) 1754-1760.
Picard Tools—By Broad Institute. sur <http://broadinstitute-.github.io/picard.> Accessed on June 16th, 2016.
Milne et al., Using Tablet for visual exploration of second-generation sequencing data, Brief. Bioinf. 14 (2013) 193-202.
F. Peyresaubes et al., Immuno-capture of UVDE generated 3'-OH ends at UV photoproducts, DNA Repair (Amst.) 36 (2015) 156-161.

What is claimed is:

1. A method for quantifying double-strand breaks in a sample comprising sample DNA molecules, the method comprising:
   (a) contacting the sample with a DNA ligase and a DNA polymerase to (i) allow the reparation of the totality of the DNA nick and DNA gap that are present in the sample DNA molecules, (ii) inhibit the amplification of the sample DNA molecules and (iii) obtain a first DNA mixture comprising first DNA molecules having a 3'-OH free terminus, wherein the 3'OH free terminus of the first DNA molecules is from a double-strand break present in in the sample DNA molecules;
   (b) contacting the first DNA mixture with a terminal deoxynucleotidyl transferase (TdT) and a substrate of the TdT, said substrate comprising a nucleotide having a label, under conditions so as to allow the incorporation of the nucleotide at the 3'-OH free terminus of the first DNA molecules to obtain a second DNA mixture comprising second DNA molecules having the incorporated nucleotide;
   (c) purifying the second DNA molecules from the second DNA mixture to obtain substantially isolated DNA molecules;
   (d) optionally amplifying, arraying and/or sequencing the substantially isolated DNA molecules obtained at step (c); and
   (e) quantifying a signal associated with the substantially isolated DNA molecules obtained at step (c), the amplification of the substantially isolated DNA molecules obtained at step (d), the array of the substantially isolated DNA molecules obtained at step (d) and/or the sequence of the substantially isolated DNA molecules obtained at step (d) to quantify and optionally locate DNA double-strand breaks in the sample.

2. The method of claim 1, wherein, prior to step (a), the sample comprises isolated sample DNA molecules.

3. The method of claim 1 lacking purifying the first DNA molecules between steps (a) and (b).

4. The method of claim 1, wherein the DNA ligase is a T4 DNA ligase and/or the DNA polymerase is a T4 DNA polymerase.

5. The method of claim 1, wherein the conditions used in step (a) comprise including adenosine triphosphate (ATP) at a concentration of less than about 10 µM in a buffer for the DNA ligase and/or for the DNA polymerase.

6. The method of claim 1, wherein the conditions used in step (a) comprise using a single buffer for contacting the sample with the DNA ligase and the DNA polymerase.

7. The method of claim 1 comprising, at step (c), positively selecting the second DNA molecules from the second DNA mixture to obtain the substantially isolated DNA molecules.

8. The method of claim 7 comprising using a silanol-based solid support to positively select the second DNA molecules from the second DNA mixture.

9. The method of claim 7, wherein the label is a radioactive isotope, an enzyme or a light-emitting entity or a prosthetic group.

10. The method of claim 9, wherein the nucleotide is a terminator nucleotide.

11. The method of claim 1 further comprising, prior to step (d), fragmenting with a fragmenting enzyme the substantially isolated DNA molecules to provide fragmented DNA molecules and, at step (d), quantifying a signal associated with the fragmented DNA molecules to quantify DNA double-strand breaks in the sample.

12. The method of claim 11, wherein the fragmenting enzyme is a double-strand endonuclease.

13. The method of claim 11 comprising using a solid support to positively select the fragmented DNA molecules comprising the incorporated nucleotide to provide isolated, fragmented and labeled DNA molecules.

14. The method of claim 13, wherein the solid support comprising an antibody specific for the label.

15. The method of claim 1 comprising, at step (d), amplifying the isolated, fragmented and labeled DNA molecules and, at step (e), quantifying the signal associated with the isolated, amplified fragmented and labeled DNA molecules to quantify and optionally localize the DNA double-strand breaks in the sample.

16. The method of claim 15 comprising using quantitative PCR to amplify the isolated, fragmented and labeled DNA molecules.

17. The method of claim 1 comprising, at step (d), sequencing the isolated, fragmented and labeled DNA molecules and, at step (e) quantifying the signal associated with the isolated, sequenced fragmented and labeled DNA molecules to quantify and optionally localize the DNA double-strand breaks in the sample.

18. The method of claim 17 comprising using next generation sequencing to sequence the isolated, fragmented and labeled DNA molecules.

19. The method of claim 5, wherein the conditions used in step (a) comprise including ATP at the concentration of about 1 µM in the buffer for the DNA ligase and/or for the DNA polymerase.

* * * * *